United States Patent
Chung et al.

(10) Patent No.: US 8,831,177 B2
(45) Date of Patent: Sep. 9, 2014

(54) APPARATUS AND METHOD FOR MANAGING RADIATION DOSES AND RECORDING MEDIUM FOR IMPLEMENTING THE SAME

(75) Inventors: Myung-Jin Chung, Seoul (KR); Yong Kee Hwang, Seoguipo (KR)

(73) Assignee: General Electric Company, Schenectady, NY (US)

( * ) Notice: Subject to any disclaimer, the term of this patent is extended or adjusted under 35 U.S.C. 154(b) by 357 days.

(21) Appl. No.: 13/303,422

(22) Filed: Nov. 23, 2011

(65) Prior Publication Data
US 2012/0300912 A1 Nov. 29, 2012

(30) Foreign Application Priority Data
May 27, 2011 (KR) .................. 10-2011-0050570

(51) Int. Cl.
*H05G 1/42* (2006.01)
*A61B 6/00* (2006.01)

(52) U.S. Cl.
CPC ............ *A61B 6/5217* (2013.01); *A61B 6/5294* (2013.01); *A61B 6/588* (2013.01)
USPC .............................. 378/97; 378/62; 378/207

(58) Field of Classification Search
CPC ..... G06F 19/321; G06F 19/322; G06Q 50/24; G06T 7/0012; G06T 11/003
USPC ..................... 378/62, 97, 108, 207
See application file for complete search history.

(56) References Cited

U.S. PATENT DOCUMENTS

| | | |
|---|---|---|
| 4,020,329 A | 4/1977 | Church et al. |
| 4,455,609 A | 6/1984 | Inamura et al. |
| 5,767,520 A | 6/1998 | Donahue et al. |
| 7,022,998 B2 | 4/2006 | Lightfoot et al. |
| 8,009,804 B2 | 8/2011 | Siljamaki et al. |
| 2002/0074501 A1 | 6/2002 | Isoda et al. |
| 2003/0111612 A1 | 6/2003 | Lightfoot et al. |
| 2008/0292055 A1* | 11/2008 | Boone ............................. 378/97 |

* cited by examiner

*Primary Examiner* — Courtney Thomas
(74) *Attorney, Agent, or Firm* — Armstrong Teasdale LLP

(57) ABSTRACT

An apparatus for managing radiation doses is provided. The apparatus includes an information extraction unit configured to extract information about a patient to be examined, information about an image acquired by examining a bodily region of the patient using a radiographic apparatus, and information about the examination performed by the radiographic apparatus, a radiation dose calculation unit configured to calculate, using the image information, an effective dose generated by the radiographic apparatus when acquiring the image, and a dose data storage unit configured to store effective dose data in a database, the effective dose data including the calculated effective dose, the patient information, and the examination information.

20 Claims, 4 Drawing Sheets

APPARATUS AND METHOD FOR MANAGING RADIATION DOSES AND RECORDING MEDIUM FOR IMPLEMENTING THE SAME

CROSS REFERENCE TO RELATED APPLICATIONS

This application claims the benefit of Korean Patent Application No. 10-2011-0050570 filed May 27, 2011, which is hereby incorporated by reference in its entirety.

BACKGROUND OF THE INVENTION

The present invention relates to management of radiation doses and, more particularly, to an apparatus and method for managing radiation doses which extract image information about a captured image acquired by a radiographic apparatus, information about a patient to be examined, and examination information, calculate an Effective Dose (ED) based on the extracted information, and manage a radiation exposure dose for each patient. The present invention is also related to a recording medium which is used to implement the same.

In general, in order to perform radiation treatment in a hospital, many systems or apparatuses may be used. These systems and apparatuses include an Electronic Medical Record (EMR) system, an Order Communication System (OCS), a Picture Archiving and Communication System (PACS), a Radiation Treatment Planning (RTP) system, and radiation treatment equipment (e.g., a Linear Accelerator (LINAC)).

An OCS is a system that includes a database for storing various types of medical information and the examination data of patients and transfers prescriptions, which were issued by doctors after examining the patients, to individual corresponding treatment departments over a communication network.

An EMR system is a system that is configured to store and search electronic medical records.

A PACS is a system that can store images, captured by at least one medical imaging system, such as Computed Tomography (CT) equipment, Magnetic Resonance Imaging (MRI) equipment, Positron Emission Tomography (PET) equipment, a CT Simulator, or Computed Radiography (CR) equipment, in computer file form and transfer the images. The PACS has been adopted by most of middle or higher class hospitals.

An RTP system is a system that uses a program to formulate plans for radiation treatment for patients. An RTP system formulates radiation treatment plans, that is, prepares radiation treatment plan information, and performs the calculation and examination of radiation doses.

Radiation treatment equipment is an apparatus that actually performs radiation treatment on patients in accordance with radiation treatment plans that were made by the RTP system.

When radiation treatment is applied to a patient using the above-described apparatuses, a radiation dose to which the patient is exposed (Effective Dose (ED)) may be an important variable. In other words, in radiation therapy, it is necessary to receive feedback about the radiation dose to which a patient was exposed, to calculate an allowable radiation dose for the patient in subsequent radiation treatments, and to enable an RTP system to formulate a radiation treatment plan for the patient based on the calculated radiation dose.

However, the radiation treatment equipment is not provided with a device for calculating radiation doses for patients, and therefore there is no provision for a method of estimating the allowable radiation doses for patients receiving radiation treatments.

Accordingly, there is a need for a system that is capable of, when administering radiation treatment, calculating an ED for each patient and managing ED data in an integrated fashion.

SUMMARY OF THE INVENTION

The embodiments described herein include an apparatus and method for managing radiation doses which extract image information about an image captured by a radiographic apparatus, information about a patient to be examined, and examination information, calculate an Effective Dose (ED) based on the extracted information, and manage a radiation exposure dose for each patient. The embodiments described herein also include a recording medium which is used to implement the same.

In accordance with a one embodiment, there is provided an apparatus for managing radiation doses, including an information extraction unit for extracting information about a patient to be examined, information about an image acquired by examining a bodily region of the patient with a radiographic apparatus, and information about the examination performed by the radiographic apparatus. The apparatus further includes a radiation dose calculation unit for calculating, using the image information, an effective dose generated by the radiographic apparatus when acquiring the image, and a dose data storage unit for storing effective dose data in a database, the effective dose data including the calculated effective dose, the patient information and the examination information.

The image may be a Digital Imaging and Communication in Medicine (DICOM) standard image containing a header, and the information extraction unit may extract the image information from the header of the image.

The image information may include at least one of an X-ray tube current value, a voltage output value of an X-ray generator and a Source Image receptor Distance (SID) value.

The radiation dose calculation unit may determine one or more conversion coefficients based at least on the SID value used in acquiring the image, obtain an entrance surface dose based on the X-ray tube current value, the voltage output value, and the one or more conversion coefficients, and calculate the effective dose based on the entrance surface dose and a conversion coefficient, the conversion coefficient being determined based on the body region of the patient.

The radiation dose calculation unit may calculate the entrance surface dose based on the following equation:

$$ESD = \alpha \times TCP \times TV^\beta$$

where ESD is the entrance surface dose in uGy, TCP is the X-ray tube current in mAs, TV is the voltage output value in kVp, and $\alpha$ and $\beta$ are the conversion coefficients.

The image information further may include information about the type of radiographic apparatus and also about a manufacturer thereof, and the one or more conversion coefficients may be determined based on the SID value, the type of radiographic apparatus and the manufacturer thereof.

In accordance with another embodiment, there is provided a method for managing radiation dose, comprising extracting information about a patient to be examined, information about an image acquired by examining a bodily region of the patient with a radiographic apparatus, and information about the examination performed by the radiographic apparatus. The method further includes calculating, using the image information, an effective dose being generated by the radiographic apparatus in acquiring the image, and storing effective dose data in a database, the effective dose data including the calculated effective dose, the patient information and the examination information.

The image may be a DICOM standard image containing a header, and the extracting the image information may include extracting the image information from the header of the image.

The image information may include at least one of an X-ray tube current value, a voltage output value of an X-ray generator and an SID value.

The method may further include determining one or more conversion coefficients based at least on the SID value used in acquiring the image, acquiring an entrance surface dose based on the X-ray tube current value, the voltage output value, and the one or more conversion coefficients, and calculating the effective dose based on the entrance surface dose and a conversion coefficient, the conversion coefficient being determined based on the body region of the patient.

Extracting the image information may further include determining whether the SID value is stored in the header of the image, and, if it is determined that the SID value is not stored in the header of the image, extracting a default value for the SID value pre-set in the radiographic apparatus.

In accordance with still another embodiment, there is provided a computer readable storage medium storing a computer program comprising computer-implementable instructions for carrying out the method(s) above.

BRIEF DESCRIPTION OF THE DRAWINGS

The above and other objects and features of the embodiments described herein will become apparent from the following description of exemplary embodiments given in conjunction with the accompanying drawings, in which.

DETAILED DESCRIPTION OF THE INVENTION

Hereinafter, exemplary embodiments of will be described in detail with reference to the accompanying drawings so that they can be readily implemented by those skilled in the art.

An apparatus and method for calculating EDs based on ESDs and managing the EDs will be described in detail below with reference to the accompanying drawings.

Figures 1, 2:
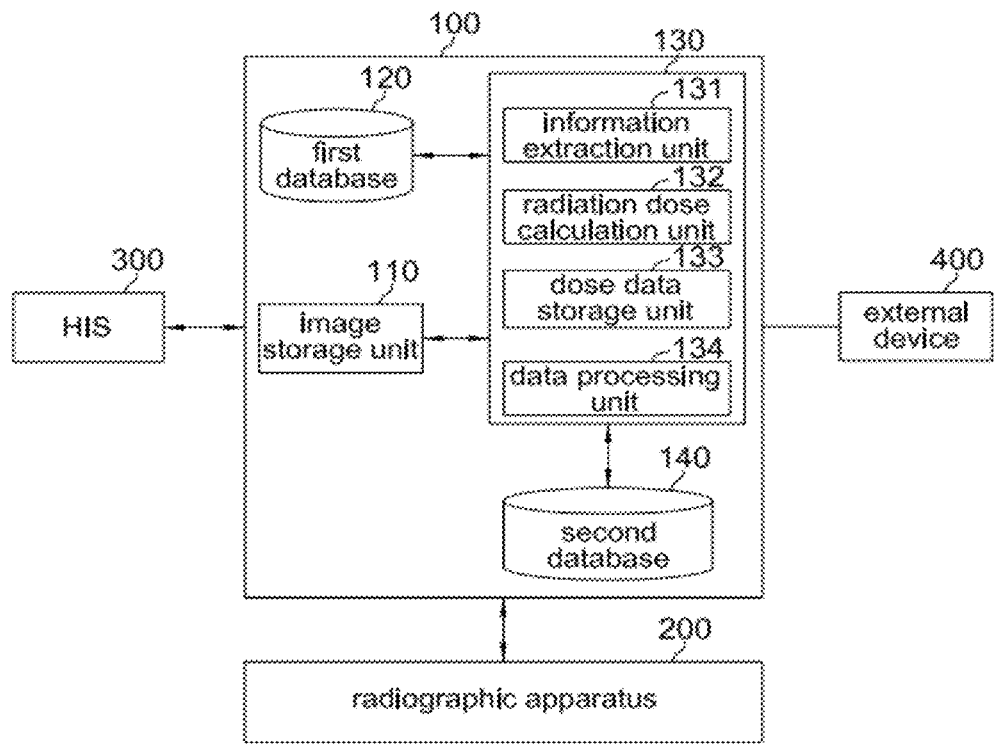
FIG. 1 is a block diagram showing the overall configuration including an exemplary apparatus for managing radiation doses.
FIG. 2 is a table showing the structure of the header of a DICOM image.

FIG. 1 is a block diagram showing the overall configuration including an exemplary apparatus for managing radiation doses.

As shown in FIG. 1, a PACS 100 may be connected to a radiographic apparatus 200, a Hospital Information System (HIS) 300, and an external device 400 over a communication network (not shown).

Furthermore, the PACS 100 may include an image storage unit 110, a first database 120, an apparatus 130 for managing radiation doses, and a second database 140.

The radiographic apparatus 200 may include CR equipment, Digital Radiography (DR) equipment, CT equipment, Multi-Detector Computed Tomography (MDCT) equipment, PET equipment, angio-fluoroscopy equipment, angiography equipment, mammographic X-ray equipment, etc.

CR equipment is a system that acquires an image by passing a body through a reader, instead of performing development, using an image plate (IP), instead of the cassette of a general X-ray imaging apparatus. DR equipment is a system that acquires an image immediately after capturing it using a detector capable of acquiring images. CT equipment is a computed tomography system that emits X rays over a short period of time and acquires a tomogram of a bodily region. MDCT equipment is a system that acquires a three-dimensional color image by emitting high-speed X rays at one time and capturing 64 tomograms. PET equipment is a positron emission tomography system that is used to acquire an image of a path through which a radioactive medicine propagates across a living body or an image of spots where radioactive medicine has accumulated after the radioactive medicine has been injected into a blood vessel. A contrast agent through which radioactive rays do not pass is injected into a body, and then a specific region or organ of the body is selectively captured using radiation fluoroscopy. The PET equipment may be used to observe blood vessels against surrounding tissues after injecting a contrast agent into a blood vessel. That is, the PET equipment is used to diagnose the anatomical structure of a specific blood vessel, determine the presence of a lesion, and determine a physiological state.

The HIS 300 is a system that manages information about patients to be examined (for example, the names, IDs and birth dates of patients) and examination information (for example, examination dates, examination codes, and examination numbers). The HIS 300 may provide patient information and examination information in response to a request from the PACS 100 or provide radiation prescription information to the radiographic apparatus 200. Examples of the HIS 300 include an HIS, an OCS, and a Radiology Information System (RIS).

The external device 400 requests and receives an ED for each period for a specific patient while operating in conjunction with the PACS 100 over a communication network. An example of the external device 400 is an EMR System.

The image storage unit 110 may receive an image captured by the radiographic apparatus 200, convert it into Digital Imaging and Communication in Medicine (DICOM) format, and store it. The resulting DICOM image contains a DICOM header.

A DICOM header, as shown in FIG. 2, may include image information, information about the radiographic apparatus 200, examination information about a radiographic examination, and patient information about a personal history of a patient to be examined. The image information may include the voltage output of an X-ray generator (KVP), X-ray tube current and a Source Image Receptor Distance (SID) value when an image is captured using the radiographic apparatus 200. The SID value is the distance between the part of the radiographic apparatus 200, which emits radioactive rays, and a patient while radiographic capturing is being performed.

The first database 120 may store information about a patient to be examined and examination information that are provided by the HIS 300. The information about a patient to be examined may include the patient's name, ID, and birth date, and the examination information may include the date and hour of an examination, an examination code, and an examination number.

The apparatus 130 for managing radiation doses may extract image information about an image acquired by examining a bodily region of a patient to be examined using the radiographic apparatus 200. The apparatus 130 may also extract information about the radiographic apparatus 200 from the header of a DICOM image stored in the image storage unit 110, extract patient information about the patient to be examined and examination information from the first database 120, and then calculate an Effective Dose (ED) based on radiographic capturing using the examination information and the image information. The calculated ED may be stored in the second database 140, and be managed, for example, for each patient.

For this purpose, the apparatus 130 may include an information extraction unit 131 for extracting patient information about the personal history of the patient, examination information about the radiographic examination, and image information acquired from an image captured by the radiographic apparatus 200. The apparatus 130 may also include a radiation dose calculation unit 132 for calculating an ED that is generated when the image is acquired by the radiographic apparatus 200, using the image information, a dose data storage unit 133 for storing the ED in the second database 140, and a data processing unit 134 for searching the second database 140 and then providing search result data in response to a request from the external device 400. Please replace paragraph [0028] with the following amended paragraph.

The information extraction unit 131 is means for extracting patient and examination information stored in the first database 120, as well as image information from the header of a DICOM image. The information extraction unit 131 may extract patient data, such as a patient's ID, name and birth date, and study data, such as an examination date, an examination code and an examination number, by searching the first database 120. The information extraction unit may extract image information by searching the header of a DICOM image stored in the image storage unit 110. Although the image information may include information about the type of radiographic apparatus 200 and the manufacturer thereof, the X-ray tube current, the voltage output of an X-ray generator, and an SID value, it is not limited thereto.

Examples of the image information extracted by the information extraction unit 131 are illustrated in the following Tables 1 and 2.

TABLE 1

| DICOM Tag | Attribute Name | Description |
| --- | --- | --- |
| 0018,0060 | KVP | |
| 0018,1150 | Exposure Time | |
| 0018,1151 | X-ray Tube Current | |
| 0018,1152 | Exposure | Tube current-time product in mAs |
| 0018,1153 | Exposure in mAs | The exposure expressed in mAs, for example, calculated from Exposure Time and X-ray Tube Current. |
| 0018,115E | Image Area Dose Product | Kerma-area product in dGy-cm$^2$ |
| 0018,1404 | Exposure on Plate | Number of exposures on plate |
| 0018,1405 | Relative X-ray Exposure | Relative exposure on plate |
| 0018,6000 | Sensitivity | Detector Sensitivity |
| 0018,0302 | Entrance Dose | Entrance dose on the patient [dGy] |

TABLE 2

| DICOM Tag | Attribute Name | Description |
| --- | --- | --- |
| 0008,0060 | Modality | Information about type of equipment (e.g., CT, CR, DR, or MR equipment) |
| 0008,0070 | Manufacturer | Information about manufacturer of equipment |
| 0008,1010 | Station Name | Unique station name of equipment |
| 0008,1090 | Manufacturer's Model Name | Model name of equipment |

The radiation dose calculation unit 132 calculates an Entrance Surface Dose (ESD) using the examination information and the image information provided by the information extraction unit 131, and converts the ESD using preset conversion factors, thereby calculating an ED.

An ESD may be calculated using, for example, the following Equation 1:

$$ESD = \alpha \times TCP \times TV^\beta \quad (1)$$

where TCP is the X-ray tube current in mAs when the radiographic apparatus 200 captures an image, and TV is the voltage output of the X-ray tube in kVp, which can be extracted from the header of a DICOM image.

Figure 3A:
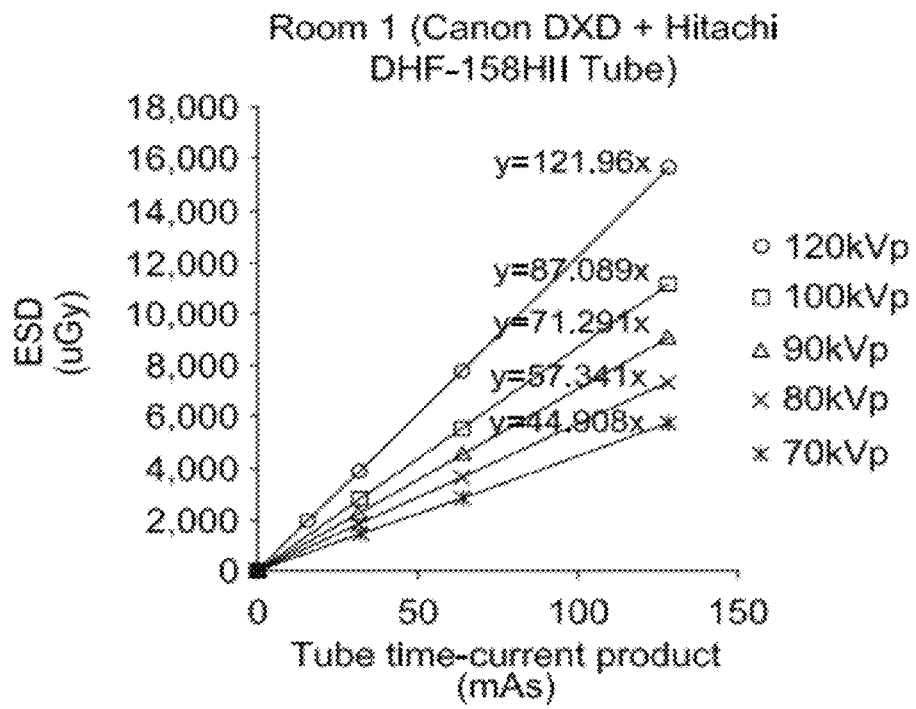
FIG. 3a is a graph illustrating the correlations between X-ray tube currents, based on the voltage outputs of an X-ray generator, and ESDs.

Based on the above Equation 1, the correlations between the currents in milliamps (mAs) and the ESDs in micrograys (uGy) for respective voltages in peak kilovoltages (kVp) are shown in FIG. 3a. FIG. 3a shows the correlations between currents and ESDs for respective voltages that were obtained when images were captured using Canon's Digital X-ray System, which is the radiographic apparatus 200 in the exemplary embodiment.

Figure 3B:
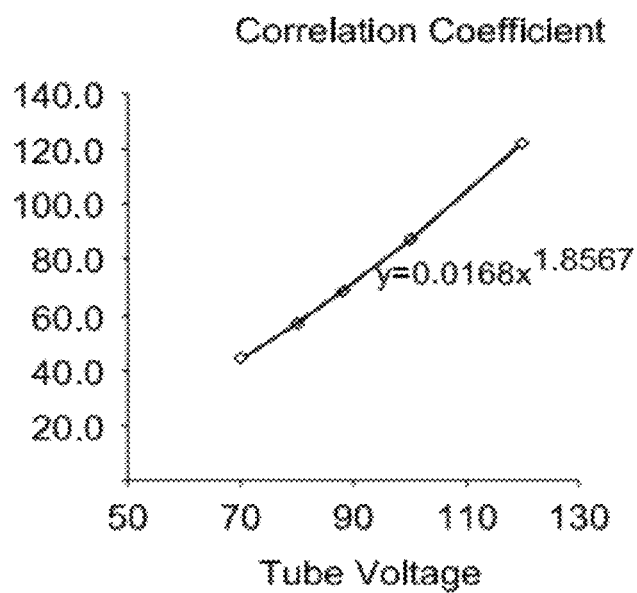
FIG. 3b is a graph illustrating the correlation between SID values and conversion coefficients.

Furthermore, in Equation 1, α and β are conversion coefficients that are used to calculate an ESD. When the result values of FIG. 3a are illustrated in terms of correlation between the voltages and the slope values, calculated for the respective voltages in FIG. 3a, so as to calculate the conversion coefficients, FIG. 3b is obtained. For example, in FIG. 3b, when the SID value is 110 cm, α may be 0.0168 and β may be 1.8567. Such conversion coefficients α and β may be obtained by, for example, experiments based on the related international standard(s), and may be set in the apparatus 130 for managing radiation doses. Such conversion coefficients vary depending on the type of radiographic apparatus 200 and the manufacturer thereof as well as the SID value.

Furthermore, the equation that is used to calculate such an ESD is not necessarily limited to Equation 1, and it will be apparent to those skilled in the art that it may be modified into various forms, for example, a linear function, a log function or the like, when needed.

Figure 4:
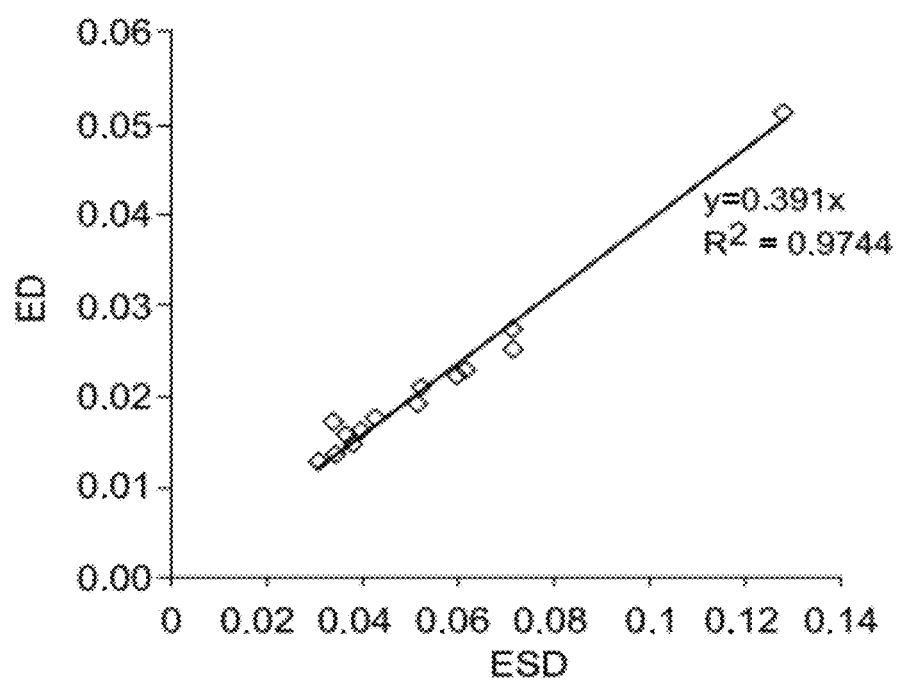
FIG. 4 is a graph illustrating the correlation between ESDs and EDs.

After the ESD has been calculated using the above process, an ED can be calculated using a conversion factor. The conversion factor may be calculated based on data obtained by collecting the conditions of a plurality of actual patients, that is, patient information, and ESDs and EDs obtained by performing measurements. Furthermore, conversion factors are set for respective regions to be captured in the apparatus 130 for managing radiation doses. That is, based on the data shown in the following Table 3, ESDs and EDs have a linear correlation, as shown in FIG. 4. Using this, a conversion factor for each examination modality or for each bodily region may be calculated.

TABLE 3

| Plate No. | Weight (kg) | Height (cm) | TCP (mAs) | DAP (dGy · cm²) | ESD (mGy) | ED (mSy) |
|---|---|---|---|---|---|---|
| 1 | 53 | 164 | 1.43 | 0.365 | 0.031 | 0.0129 |
| 2 | 57 | 162 | 1.60 | 0.409 | 0.035 | 0.0139 |
| 3 | 74 | 178 | 1.70 | 0.434 | 0.037 | 0.0143 |
| 4 | 82 | 168 | 2.83 | 0.722 | 0.062 | 0.0227 |
| 5 | 82 | 176 | 2.76 | 0.704 | 0.060 | 0.0223 |
| 6 | 75 | 177 | 2.43 | 0.620 | 0.053 | 0.0209 |
| 7 | 58 | 163 | 1.75 | 0.448 | 0.038 | 0.0152 |
| 8 | 62 | 144 | 3.30 | 0.843 | 0.072 | 0.0253 |
| 9 | 60 | 162 | 1.61 | 0.412 | 0.035 | 0.0139 |
| 10 | 65 | 177 | 1.95 | 0.498 | 0.043 | 0.0176 |
| 11 | 52 | 170 | 1.68 | 0.429 | 0.037 | 0.0157 |
| 12 | 45 | 151 | 1.56 | 0.399 | 0.034 | 0.0173 |
| 13 | 62 | 159 | 1.58 | 0.403 | 0.034 | 0.0132 |
| 14 | 47 | 155 | 1.72 | 1.440 | 0.038 | 0.0152 |
| 15 | 72 | 173 | 5.87 | 0.500 | 0.128 | 0.0512 |
| 16 | 77 | 164 | 2.39 | 0.612 | 0.052 | 0.0191 |
| 17 | 46 | 155 | 1.95 | 0.498 | 0.043 | 0.0175 |
| 18 | 56 | 164 | 1.83 | 0.467 | 0.040 | 0.0164 |
| 19 | 52 | 154 | 1.76 | 0.450 | 0.038 | 0.0148 |
| 20 | 74 | 169 | 3.31 | 0.845 | 0.072 | 0.0274 |

The dose data storage unit 133 may store the ED, calculated by the radiation dose calculation unit 132, and the patient information in the second database 140 in association with each other.

The data processing unit 134, in response to a request from the external device 400 connected over a communication network, may search the second database 140, create search result data, and then provide it to the external device 400. That is, when a patient ID is received from the external device 400, the data processing unit 134 may search the second database 140 for an ED corresponding to the patient ID using the patient ID and provide it to the external device 400.

The process in which the apparatus 130 for managing radiation doses, which has the above-described configuration, manages a patient's radiation dose will now be described with reference to FIG. 5.

Figure 5:
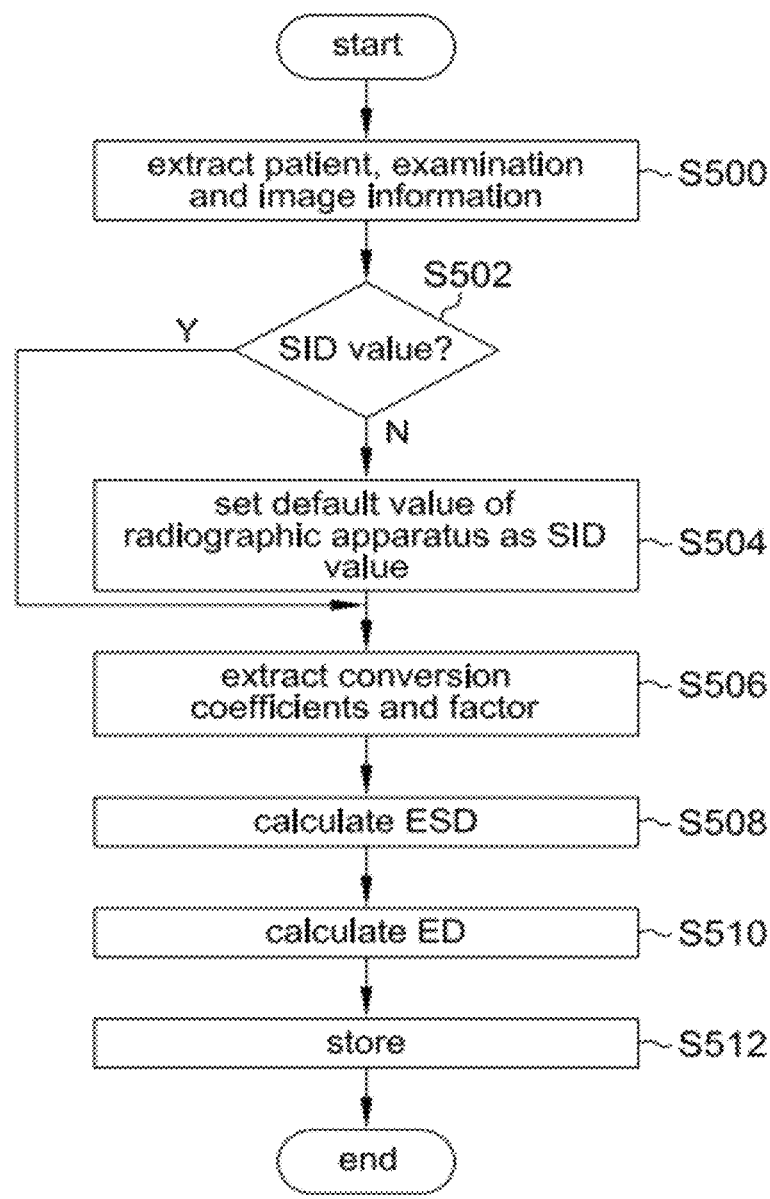
FIG. 5 is a flowchart illustrating an exemplary process in which the apparatus for managing radiation doses calculates an ED.

FIG. 5 is a flowchart illustrating an exemplary process in which the apparatus for managing radiation doses calculates an ED.

As shown in FIG. 5, first, the apparatus 130 for managing radiation doses not only extracts patient information about a patient to be examined and examination information about an examination performed by the radiographic apparatus 200 by searching the first database 120 using the information extraction unit 131, but also extracts image information by searching the header of a DICOM image stored in the image storage unit 110 at step S500. The image information may include, for example, the X-ray tube current, the voltage output of the X-ray generator and the SID value when the image was captured.

When the image information is extracted, the information extraction unit 131 determines whether an SID value is present in the header of the DICOM image at step S502. If, as a result of the determination at step S502, an SID value is not present, the information extraction unit 131 may extract a default value, set in the radiographic apparatus 200, as the SID value at step S504.

Thereafter, the information extraction unit 131 extracts conversion coefficients based on the SID value and conversion factors for respective regions to be captured at step S506, and provides the extracted conversion factors, conversion coefficients, and the X-ray tube current and the voltage output of the X-ray generator, which are contained in the image information, to the radiation dose calculation unit 132.

Thereafter, the radiation dose calculation unit 132 calculates an ESD by applying the X-ray tube current and the voltage output of the X-ray generator, which are contained in the image information and the conversion coefficients, to Equation 1 at step S508, and then calculates an ED by performing an operation on the ESD and the conversion factor at step S510.

Thereafter, the dose data storage unit 133 stores the patient information and the examination information in the second database 140 in association with the calculated ED at step S512.

According to the embodiments described herein, it is possible to not only determine a radiation exposure dose for each patient to be examined but also control a radiation exposure dose in later radiographic examination based on the determined radiation exposure dose because the embodiments described herein are configured to calculate and manage an ED for each patient to be examined.

Furthermore, the embodiments described herein have the advantage of protecting a patient from harm attributable to radioactive rays by blocking unnecessary radiographic examination because the embodiments described herein may be used to induce a patient to go through an examination using non-X ray equipment based on a radiation exposure dose.

Moreover, the embodiments described herein have the advantage of acquiring an image using a low radiation dose because the embodiments described herein may be used to easily compare and determine the radiation exposure doses and image qualities of respective X-ray apparatuses.

While the invention has been shown and described with respect to exemplary embodiments, it will be understood by those skilled in the art that various changes and modifications may be made without departing from the spirit and scope of the invention as defined in the following claims.

What is claimed is:

1. An apparatus for managing radiation doses, comprising:
an information extraction unit configured to extract information about a patient to be examined, information about an image acquired by examining a bodily region of the patient using a radiographic apparatus, and information about the examination performed by the radiographic apparatus;
a radiation dose calculation unit configured to calculate, using the image information, an effective dose generated by the radiographic apparatus when acquiring the image; and
a dose data storage unit configured to store effective dose data in a database, the effective dose data including the calculated effective dose, the patient information, and the examination information.

2. The apparatus of claim 1, wherein the image is a Digital Imaging and Communication in Medicine (DICOM) standard image containing a header, and the information extraction unit is configured to extract the image information from the header of the image.

3. The apparatus of claim 2, wherein the image information includes at least one of an X-ray tube current value, a voltage output value of an X-ray generator, and a Source Image receptor Distance (SID) value.

4. The apparatus of claim 3, wherein the radiation dose calculation unit is configured to:
determine at least one conversion coefficient based at least on the SID value used in acquiring the image;
obtain an entrance surface dose based on the X-ray tube current value, the voltage output value, and the at least one conversion coefficient; and calculate the effective dose based on the entrance surface dose and a conversion coefficient of the at least one conversion coefficient, the conversion coefficient determined based on the body region of the patient.

5. The apparatus of claim 4, wherein
the radiation dose calculation unit is configured to calculate the entrance surface dose based on the following equation:

$$ESD = \alpha \times TCP \times TV^\beta$$

where ESD is the entrance surface dose in micrograys, TCP is the X-ray tube current in milliamps, TV is the voltage output value in peak kilovoltages, and $\alpha$ and $\beta$ are the conversion coefficients.

6. The apparatus of claim 4, wherein the image information further includes information about a type of radiographic apparatus and a manufacturer thereof, and
the at least one conversion coefficient is determined based on the SID value, the type of radiographic apparatus, and the manufacturer thereof.

7. A method for managing radiation dose, comprising:
extracting information about a patient to be examined, information about an image acquired by examining a bodily region of the patient with a radiographic apparatus, and information about the examination performed by the radiographic apparatus;
calculating, using the image information, an effective dose being generated by the radiographic apparatus in acquiring the image; and
storing effective dose data in a database, the effective dose data including the calculated effective dose, the patient information, and the examination information.

8. The method of claim 7, wherein the image is a Digital Imaging and Communication in Medicine (DICOM) standard image containing a header, and extracting the image information includes extracting the image information from the header of the image.

9. The method of claim 8, wherein the image information includes at least one of an X-ray tube current value, a voltage output value of an X-ray generator, and a Source Image receptor Distance (SID) value.

10. The method of claim 9, further comprising:
determining at least one conversion coefficient based at least on the SID value used in acquiring the image;
acquiring an entrance surface dose based on the X-ray tube current value, the voltage output value, and the at least one conversion coefficient; and
calculating the effective dose based on the entrance surface dose and a conversion coefficient of the at least one conversion coefficient, the conversion coefficient determined based on the body region of the patient.

11. The method of claim 9, wherein extracting the image information further includes:
determining whether the SID value is stored in the header of the image; and
if it is determined that the SID value is not stored in the header of the image, extracting a default value for the SID value pre-set in the radiographic apparatus.

12. The method of claim 10, wherein acquiring an entrance surface dose comprises calculating the entrance surface dose based on the following equation:

$$ESD = \alpha \times TCP \times TV^\beta$$

where ESD is the entrance surface dose in micrograys, TCP is the X-ray tube current in milliamps, TV is the voltage output value in peak kilovoltages, and $\alpha$ and $\beta$ are the conversion coefficients.

13. The method of claim 10, wherein the image information further includes information about a type of radiographic apparatus and a manufacturer thereof, and
the at least one conversion coefficient is determined based on the SID value, the type of radiographic apparatus, and the manufacturer thereof.

14. A computer readable storage medium storing a computer program comprising computer-implementable instructions for:
extracting information about a patient to be examined, information about an image acquired by examining a bodily region of the patient with a radiographic apparatus, and information about the examination performed by the radiographic apparatus;
calculating, using the image information, an effective dose being generated by the radiographic apparatus in acquiring the image; and
storing effective dose data in a database, the effective dose data including the calculated effective dose, the patient information, and the examination information.

15. The computer readable storage medium of claim 14, wherein the image is a Digital Imaging and Communication in Medicine (DICOM) standard image containing a header, and extracting the image information includes extracting the image information from the header of the image.

16. The computer readable storage medium of claim 15, wherein the image information includes at least one of an X-ray tube current value, a voltage output value of an X-ray generator, and a Source Image receptor Distance (SID) value.

17. The computer readable storage medium of claim 16, wherein the computer readable storage medium further comprises computer-implementable instructions for:
determining at least one conversion coefficient based at least on the SID value used in acquiring the image;
acquiring an entrance surface dose based on the X-ray tube current value, the voltage output value, and the at least one conversion coefficient; and
calculating the effective dose based on the entrance surface dose and a conversion coefficient of the at least one conversion coefficient, the conversion coefficient determined based on the body region of the patient.

18. The computer readable storage medium of claim 16, wherein the computer readable storage medium further comprises computer-implementable instructions for:
determining whether the SID value is stored in the header of the image; and
if it is determined that the SID value is not stored in the header of the image, extracting a default value for the SID value pre-set in the radiographic apparatus.

19. The computer readable storage medium of claim 17, wherein the computer readable storage medium further comprises computer-implementable instructions for calculating the entrance surface dose based on the following equation:

$$ESD = \alpha \times TCP \times TV^\beta$$

where ESD is the entrance surface dose in micrograys, TCP is the X-ray tube current in milliamps, TV is the voltage output value in peak kilovoltages, and $\alpha$ and $\beta$ are the conversion coefficients.

20. The computer readable storage medium of claim 17, wherein the image information further includes information about a type of radiographic apparatus and a manufacturer thereof, and
the at least one conversion coefficient is determined based on the SID value, the type of radiographic apparatus, and the manufacturer thereof.

* * * * *